United States Patent
Day

(10) Patent No.: US 6,838,087 B1
(45) Date of Patent: Jan. 4, 2005

(54) COSMETIC COMPOSITIONS HAVING IMPROVED TACTILE AND WEAR PROPERTIES

(75) Inventor: Rupert P. Day, Derby, CT (US)

(73) Assignee: Cognis Corporation, Cincinnati, OH (US)

( * ) Notice: Subject to any disclaimer, the term of this patent is extended or adjusted under 35 U.S.C. 154(b) by 378 days.

(21) Appl. No.: 09/703,279

(22) Filed: Nov. 1, 2000

Related U.S. Application Data

(60) Provisional application No. 60/165,633, filed on Nov. 15, 1999.

(51) Int. Cl.[7] .............................. A61K 6/00; A61K 7/00; A61K 9/14; A61K 9/16
(52) U.S. Cl. ........................ 424/401; 424/489; 424/490
(58) Field of Search ................................. 424/401, 451, 424/452, 484, 485, 489, 490; 502/69

(56) References Cited

FOREIGN PATENT DOCUMENTS

| JP | 63-027501 | * | 2/1988 | ........... C08B/37/08 |
|----|-----------|---|--------|----------------------|
| JP | 63-127501 | * | 2/1988 | ........... C08B/37/08 |
| JP | 04-235906 | * | 8/1992 | ............ A61K/7/02 |
| JP | 11-124324 | * | 5/1999 | |

OTHER PUBLICATIONS

U.S. patent application Ser. No. 09/5,122,418, Nakane et al., filed Oct. 1990.*

U.S. patent application Ser. No. 09/5,945,108, Sugawara et al., filed Jun. 1996.*

U.S. patent application Ser. No. 09/5,057,542, Leuba et al., filed Oct. 1989.*

U.S. patent application Ser. No. 09/5,077,052, Franzoni et al., filed Nov. 1989.*

* cited by examiner

*Primary Examiner*—Thurman K. Page
*Assistant Examiner*—Humera N. Sheikh
(74) *Attorney, Agent, or Firm*—Aaron R. Ettelman; Steven J. Trzaska; Daniel S. Ortiz

(57) ABSTRACT

An anhydrous powder composition for use in personal care products containing a solid particulate component and chitosan having a particle size of from about 0.1 to about 50 microns.

21 Claims, No Drawings

COSMETIC COMPOSITIONS HAVING IMPROVED TACTILE AND WEAR PROPERTIES

CROSS-REFERENCE TO RELATED APPLICATIONS

This application claims the benefit of copending provisional application Ser. No. 60/165,633 filed on Nov. 15, 1999.

STATEMENT REGARDING FEDERALLY SPONSORED RESEARCH OR DEVELOPMENT

Not applicable.

BACKGROUND OF THE INVENTION

The present invention generally relates to powder cosmetic compositions having enhanced tactile and wear properties. More particularly, the present invention relates to the preparation of loose and/or compacted powder formulations containing chitosan which increase the bulk density of particulate powders in a manner which increases the surface area covered by the powder when it is applied onto a substrate and, when used in powder cosmetic compositions, imparts improved feel properties onto human skin.

It is known that some cosmetic compositions such as blushes, eye shadows, face powders or foundations are provided in the form of compacted or cast powders. These are anhydrous compositions commonly referred to as "compact powders". They mainly consist of a mixture of coloured or non-coloured powders and a fatty binder, such as an oil or a mixture of oil and wax, which are shaped by compression or by casting into a container serving as a mould. These powders are generally used by removing a small quantity of powder and then applying it to the skin by means of an applicator such as a sponge, powder puff or brush.

The preparation of binding agents in such compact powders poses various problems. The final product should be sufficiently homogeneous and compact in order to avoid the fragmentation caused especially by impact, while retaining good disintegration capacity. Moreover, the composition should have a smooth feel and should be easy to spread in a continuous manner. In addition, the binder should be compatible with pigments and specialists are familiar with the problems of degradation of certain pigments when conventional fatty binders are used.

Certain make-up compositions are also provided in the form of "loose powders", wherein the particles are neither compacted nor dispersed in a fatty continuous phase, but retain on the contrary their individuality. Such loose powders often contain a fatty substance (oil) whose role is especially to increase the smoothness of application to promote the adherence of the powder to the skin, and to allow solubilization of some active ingredients. Some loose powders may contain relatively high quantities of oil without the particles having a tendency to agglomerate. Such is the case especially for powders containing particles in the form of hollow microspheres made from synthetic thermoplastic materials. However, the formulation of such loose powders poses the above-mentioned problem relating to the degradation of certain pigments in the presence of the fatty substances conventionally used.

BRIEF SUMMARY OF THE INVENTION

The present invention is directed to an anhydrous powder composition containing: (a) a solid particulate component; and (b) a chitosan having a particle size of from about 0.01 to about 50 microns.

The present invention is also directed to a process for treating skin involving contacting the skin with a powder composition containing: (a) a solid particulate component; and (b) a chitosan having a particle size of from about 0.1 to about 50 microns.

BRIEF DESCRIPTION OF THE SEVERAL VIEWS OF THE DRAWINGS

Not applicable.

DETAILED DESCRIPTION OF THE INVENTION

Other than in the operating examples, or where otherwise indicated, all numbers expressing quantities of ingredients and/or reaction conditions are to be understood as being modified in all instances by the term "about".

The anhydrous powder composition of the present invention contains, at a minimum, two basic components, namely, a solid particulate component and, a chitosan. This powder composition may then be used as a cosmetic composition such as, for example, make-up, eyeshadow and lipstick, a foot powder, a deodorant, and the like.

There are a number of suitable solid particulate components which may be employed in the present invention including, but not limited to, talc, micas, modified or unmodified starch, silica, alumina, boron nitride, kaolin, zinc and titanium oxides, stearates, precipitated calcium carbonates, magnesium carbonate or hydrocarbonate, metallic soaps derived from a carboxylic organic acid having from 8 to 22 carbon atoms, synthetic polymer or (copolymer) powders such as polyethylenes, polyacrylates, polymethacrylates, polyesters, polyamides, and the like, and powders in the form of hollow microspheres made from thermoplastic materials whose hollow part may contain a gas.

Chitosan is derived from chitin by deacetylation. Chitin itself is typically obtained from conventional sources such as crustacean outer shells and fungal mycelial mats. Chitin and chitosan refer to a family of compounds that exhibit widely differing physical and chemical properties. These differences are due primarily to the products' varying molecular weights, degrees of acetylation and presence of contaminants such as covalently bound, species-specific proteins, single amino acid and; inorganic contaminants.

Though any type of chitosans, in general, may be used by the present invention, particularly preferred chitosans are those having molecular weights ranging from about 1,000 to about 25,000,000, and preferably from about 500,000 to about 5,000,000 g/mol, and a particle size of from about 0.1 to about 50 microns, preferably from about 0.1 to about 40, and most preferably from about 0.1 to about 10 microns.

According to one embodiment of the present invention, there is provided an anhydrous powder composition containing: (a) from about 10 to about 95% by weight, preferably from about 50 to about 95% by weight, and most preferably from about 70 to about 95% by weight of a solid particulate component; and (b) from about 0.01 to about 10% by weight, preferably from about 0.1 to about 5% by weight, and most preferably from about 0.1 to about 3% by weight of a chitosan, all weights being based on the weight of the composition.

The anhydrous powder composition described above can either be used by itself as, for example, a cosmetic foundation for human skin, or it may be combined with other additives for various other applications.

For instance, in order to impart color onto a substrate, such as human skin, treated therewith, pigments can be added to the base composition in an amount of from about 0.01 to about 60% by weight, preferably from about 2 to about 20% by weight, and most preferably from about 5 to about 20% by weight, based on the weight of the composition.

Suitable pigments may be chosen from inorganic and/or organic pigments, and/or pearlescent pigments. Examples of inorganic pigments include, but are not limited to, titanium dioxide, black, yellow, red and brown iron oxides, manganese violet, ultramarine violet, ultramarine blue, chromium oxide, hydrated chromium oxide and ferric blue.

Organic pigments which may be employed include, but are not limited to, D & C red No. 3, D & C red No. 6, D & C red No. 7, D & C red No. 9, D & C red No. 13, D & C red No. 19, D & C red No. 21, D & C red No. 27, D & C red No. 30, D & C red No. 36, carbon black and lacquers based on carmine.

Suitable pearlescent pigments include, but are not limited to, white pearlescents such as mica coated with titanium oxide or bismuth oxychloride, mica-titanium coloured with iron oxides, mica-titanium coloured with ferric blue, and the like.

Another auxiliary component which may be included, particularly in the event that a compacted rather than loose cosmetic composition is being formed is a binder/emollient which acts to both further enhance compaction/binding of the solid particulate component and provide emolliency properties onto skin treated therewith.

Suitable binder/emollients which may be employed by the present invention include, but are not limited to, fatty acids, fatty alcohols, esters of fatty acids and fatty alcohols, Guerbet alcohols, waxes, silicones, alkanes, vegetable oils, mineral oils, animal oils such as lanolin, insect oils, humectants, glycols, starches, sugars, excipients, plasticizers, aromatic hydrocarbons, deionized water, aliphatic hydrocarbons, cyclic hydrocarbons, and the like.

In the event that a binder/emollient is employed, it can be present in the composition in an amount of from about 0.05 to about 50% by weight, preferably from about 1 to about 10% by weight, and most preferably from about 3 to about 8% by weight, based on the weight of the composition.

Various standard additives may also be incorporated into the invention including, but not limited to, preservatives; antiseptics such as trichlorodiphenyl ethers, boric acid, and the like) which are used especially in deodorant powders for the body and feet and in baby powders; astringent agents which are used in deodorant powders and in foot powders such as aluminum hydroxychloride and alum; antiperspirants; sunscreen agents; cicatrizing agents; anti-free radical agents; vitamins, demulcent agents; perfumes; consistency agents; anti-pruritics (anti-itch) and the like.

In the event that an additive is employed in the composition of the present invention, it will typically be present in an amount of from about 0.01 to about 50% by to weight, based on the weight of the composition.

According to another embodiment of invention, there is provided a process for treating skin involving contacting the skin with the powder composition of the present invention. The precise amount of powder composition to be applied will depend on the end use of the product and can be easily determined by those skilled in the art.

The powder compositions of the present invention can be prepared in any conventional manner. For example, for compacted powders all of the components may be mixed and then compacted using a press. For cast powders, the components can be mixed and suspended in a solvent. This mixture is then cast into a form and the solvent evaporated therefrom. For loose powders, the components can be mixed together and then ground up.

The present invention will be better understood from the examples which follow, all of which are intended for illustrative purposes only and are not meant to unduly limit the scope of the invention in any way.

EXAMPLES

Ingredient List
HYDAGEN®=chitosan
SUNSIL®=chitosan and silica
GERMALL®=diazolidiny urea
ELESTAB®=chlorphenesin
MYRITOL® 331=cocoglyceride
MYRITOL PC®=propylene glycol dicaprylate/dicaprate
CETIOL PGL®=hexyldecanol and hexyldecyl laurate
CETIOL CC®=dicaprylyl carbonate Example 1

A loose powder composition was prepared containing the following components:

| Component | % by weight |
|---|---|
| talc | 93.95 |
| zinc stearate | 5.00 |
| chitosan | 0.50 |
| preservative | 0.55 |
| | 100.00% |

The talc and zinc stearate were added to an blender and blended for 2 minutes on high speed (grind). The preservative was then added and blended, at the same speed, for an additional 2 minutes. The chitosan was then added and also blended, at the same speed, for 2 minutes.

It was observed that the chitosan appeared to be effectively dispersed throughout the loose powder composition and appeared to also impart a nice feel property onto human skin. Some degree of adhesion of the powder also appeared to exist.

Example 2

A powder composition was prepared containing the following components:

| Component | % by weight |
|---|---|
| talc | 70.05 |
| zinc stearate | 6.50 |
| chitosan | 0.50 |
| preservative | 0.55 |
| oil binder | 6.50 |
| color pigments | 0.90 |
| pearl pigment | 15.00 |
| | 100.00% |

The talc and zinc stearate and pigments were added to an blender and blended for 4–5 minutes on high speed (grind).

The preservative was then added and blended, at the same speed, for an additional 2 minutes. The chitosan was then added and blended, at the same speed, for 2 minutes. Half of the oil binder was then slowly added and blended for 3 minutes. The other half of the oil binder was then and blended for an additional 3 minutes. The side walls of the blender were then scraped and the mixture was then blended for an additional 4 minutes until uniform.

It was observed that the chitosan appeared to be effectively dispersed throughout the anhydrous powder composition and appeared to also impart an exceptional feel property onto human skin. An excellent degree of adhesion was also observed.

Example 3

A powder composition was prepared containing the following components:

| Component | % by weight |
| --- | --- |
| talc | 69.55 |
| zinc stearate | 6.50 |
| chitosan | 1.00 |
| preservative | 0.55 |
| oil binder | 6.50 |
| color pigments | 0.90 |
| pearl pigment | 15.00 |
| | 100.00% |

The talc and zinc stearate and color pigments were added to an blender and blended for 4–5 minutes on high speed (grind). The preservative was then added and blended, at the same speed, for an additional 2 minutes. The chitosan was then added and blended, at the same speed, for 2 minutes. Half of the oil binder was then slowly added and blended for 3 minutes. The other half of the oil binder was then and blended for an additional 3 minutes. The side walls of the blender were then scraped and the mixture was then blended for an additional 4 minutes until uniform.

It was observed that the chitosan appeared to be effectively dispersed throughout the anhydrous powder composition and appeared to also impart an exceptional feel property onto human skin. An excellent degree of adhesion also observed.

Example 4

| | Liquid MakeUp/Foundation (light coverage) | | | | | |
| --- | --- | --- | --- | --- | --- | --- |
| O/W | LMU3 % W.W | | | LMU4 Batch size in Grams | | |
| PHASE A W | | | | | | |
| Deionized water | 72.325 | 723.25 | x | 72.325 | 723.25 | x |
| Xanthan Gum (Keltrol T) | 0.20 | 2.00 | x | 0.20 | 2.00 | x |
| Veegum | 0.50 | 5.00 | x | 0.50 | 5.00 | x |
| Glycerin | 2.00 | 20.00 | x | 2.00 | 20.00 | x |
| Elestab CPN | 0.30 | 3.00 | x | 0.30 | 3.00 | x |
| Methyl-paraben | 0.20 | 2.00 | x | 0.20 | 2.00 | x |
| Thixotropic. | | | | | | |

Directions please: Shake the container and apply as needed

| | Liquid MakeUp/Foundation (light coverage) | | | | | |
| --- | --- | --- | --- | --- | --- | --- |
| O/W | LMU3 % W.W | | | LMU4 Batch size in Grams | | |
| PHASE B O | | | | | | |
| Emulgade PL 68/50 | 2.50 | 25.00 | x | 2.50 | 25.00 | x |
| Lanette O | 1.00 | 10.00 | x | 1.00 | 10.00 | x |
| Propyl-paraben | 0.10 | 1.00 | x | 0.10 | 1.00 | x |
| Cetiol CC | 5.00 | 50.00 | x | 5.00 | 50.00 | x |
| Myritol 331 | 3.50 | 35.00 | x | 3.50 | 35.00 | x |
| Cetiol J600 | 1.00 | 10.00 | x | 1.00 | 10.00 | x |
| COLOR PHASE C* | | | | | | |
| Talc Imperial BC WCD | 2.00 | 20.00 | x | 2.00 | 20.00 | x |
| Black Iron Oxide | | | | | | |
| Brown Iron Oxide | 0.325 | 3.25 | x | 0.325 | 3.25 | x |
| Brown Iron Oxide | 0.05 | 0.50 | x | 0.05 | 0.50 | x |
| TiO2 3328 | 3.50 | 35.00 | x | 3.50 | 35.00 | x |
| ACTIVES PHASE D | | | | | | |
| Sunsil 130 (CH 2%) (130CH) | | | | 0.50 | 5.00 | |
| Sunsil 130 99081701 | | | | 0.50 | 5.00 | |
| Vegeseryl HGP | 5.00 | 50.00 | x | 5.00 | 50.00 | x |
| Total | 100.000 | 1000.00 | | 100.000 | 1000.00 | |

This product has a very light, almost transparent coverage.
Manufacturing/Processing/Mixing/Procedure

PHASE A

Keltrol and Veegum were added to H2O, and then homogenized for 10–15 Minutes. The remaining phase A ingredients were then blended in. The mixture was then heated to 75 degree celcius.

PHASE B

All ingredients comprising PHASE B were then mixed together and heated to 75° C. Phase A and Phase B were then combined.

PHASE C

Phase A and Phase B were then blended in an Osterizer until uniform color was A achieved.

PHASE D

The active ingredients were then added at cooling on slow sweep. Cool and package at a pour temp. Check for specifications. pH, Viscosity and color . . . As per your in-house manufacturing procedure. Viscosity may be increased or reduced by increasing or decreasing the emulsifiers or thickeners.

Example 5

| Hair Care Dry Color formulae | 1A | 1B |
|---|---|---|
| Powder Phase | | |
| Talc 1745 USP BC | 72.95 | 72.95 |
| Zn Stearate USP D | 6.50 | 6.50 |
| Hydagen CMFP | | |
| Sunsil 130 (CH 3%) | | |
| Sunsil 130 (CH 2%) | 0.5 | 0.5 |
| Preservative Phase | | |
| Propylparaben | | |
| Methylparaben | | |
| Germall 11 | | |
| Elestab CPN | 0.20 | 0.20 |
| Color Phase | | |
| Red Iron Oxide C 7054 Extended 70/30 Blend | 0.85 | 0.85 |
| Yellow Iron Oxide C 7055 Extended 70130 Blend | | |
| Oil Binder Phase | | |
| Myritol 331 | 3.50 | |
| Myritol PC | | |
| Cetiol PGL | 0.50 | 0.50 |
| Cetiol CC | 3.50 | |
| Pearl Phase | | |
| Colorona Oriental Beige | | |
| Colorona Imperial Red | | |
| Colorona Siena | 5.00 | |
| Colorona Russet | 5.00 | |
| Colorona Passion Orange | 5.00 | |
| Henna (Dry) | | QS to color |
| Total % | 100.00 | QS to 100% |

What is claimed is:

1. A powder composition comprising a solid particulate component and from about 0.01 to about 100% by weight, based on the weight of the composition, of chitosan having a particle size of from about 0.1 to about 50 microns.

2. The composition of claim 1 wherein the solid particulate component is present in the composition in an amount of from about 10 to about 95% by weight, based on the total weight of the composition.

3. The composition of claim 1 wherein the chitosan has a molecular weight ranging from about 500,000 to about 5,000,000 g/mol.

4. The composition of claim 1 further comprising a pigment.

5. The composition of claim 4 wherein the pigment is present in the composition in an amount of from about 0.01 to about 60% by weight, based on the total weight of the composition.

6. The composition of claim 1 further comprising a binder component.

7. The composition of claim 6 wherein the binder component is present in the composition in an amount of from about 0.05 to about 50% by weight, based on the total weight of the composition.

8. The composition of claim 1 further comprising an additive selected from the group consisting of preservatives, antiseptics, astringent agents, sunscreen agents, cicatrizing agents, anti-free radical agents, vitamins, demulcent agents, perfumes, consistency agents, anti-pruritics, anti-perspirants, and mixtures thereof.

9. The composition of claim 8 wherein the additive is present in the composition in an amount of from about 0.01 to about 50% by weight, based on the total weight of the composition.

10. A powder composition comprising:
    (a) from about 70 to about 95% by weight of a solid particulate;
    (b) from about 0.01 to about 3% by weight of a chitosan having a particle size of from about 1 to about 10 microns;
    (c) from about 10 to about 20% by weight of a pigment; and
    (d) from about 3 to about 8% by weight of a binder, all weights being: based on the total weight of the composition.

11. The composition of claim 10 further comprising an additive selected from the group consisting of preservatives, antiseptics, astringent agents, sunscreen agents, cicatrizing agents, anti-free radical agents, vitamins, demulcent agents, perfumes, consistency agents, and mixtures thereof.

12. The composition of claim 11 wherein the additive is present in the composition in an amount of from about 0.01 to about 50% by weight, based on the total weight of the composition.

13. A process for treating skin comprising contacting the skin with a a powder composition containing a solid particulate component and from about 0.01 to about 10% by weight, based on she weight of the composition, of chitosan having a particle size of less than 400 microns.

14. The process of claim 13 wherein the solid particulate component is present in the composition in an amount of from about 10 to about 95% by weight, based on the total weight of the composition.

15. The process of claim 13 wherein the chitosan has a molecular weight ranging from about 500,000 to about 5,000,000.

16. The process of claim 13 further comprising a pigment.

17. The process of claim 16 wherein the pigment is present in the composition in an amount of from about 0.01 to about 60% by weight, based on the total weight of the composition.

18. The process of claim 13 further comprising a binder component.

19. The process of claim 18 wherein the binder component is present in the composition in an amount of from about 0.05 to about 50% by weight, based on the total weight of the composition.

20. The process of claim 13 further comprising an additive selected from the group consisting of preservatives, antiseptics, astringent agents, sunscreen agents, cicatrizing agents, anti-free radical agents, vitamins, demulcent agents, perfumes, consistency agents, and mixtures thereof.

21. The process of claim 20 wherein the additive is present in the composition in an amount of from about 0.01 to about 50% by weight, based on the total weight of the composition.

* * * * *